(12) United States Patent
Willimann (10) Patent No.: US 8,053,005 B2
(45) Date of Patent: Nov. 8, 2011

(54) COMPOSITION FOR CONTROLLING THE RESPIRATORY EFFECT OF INHALED POLLUTANTS AND ALLERGENS

(75) Inventor: John A Willimann, Key Biscayne, FL (US)

(73) Assignee: Global Life Technologies Corp., Chevy Chase, MD (US)

( * ) Notice: Subject to any disclaimer, the term of this patent is extended or adjusted under 35 U.S.C. 154(b) by 113 days.

(21) Appl. No.: 12/287,411

(22) Filed: Oct. 9, 2008

(65) Prior Publication Data

US 2009/0041871 A1     Feb. 12, 2009

Related U.S. Application Data

(63) Continuation-in-part of application No. 11/545,720, filed on Oct. 10, 2006, now abandoned.

(60) Provisional application No. 60/725,050, filed on Oct. 7, 2005.

(51) Int. Cl.
*A61K 36/48* (2006.01)
*A61K 36/889* (2006.01)
*A61K 36/886* (2006.01)
*A61K 36/534* (2006.01)
*A61F 13/00* (2006.01)
*A61F 9/02* (2006.01)

(52) U.S. Cl. ........ 424/757; 424/727; 424/736; 424/744; 424/747; 424/434

(58) Field of Classification Search ........................ None
See application file for complete search history.

(56) References Cited

U.S. PATENT DOCUMENTS 4,569,839 A     2/1986    Grollier et al.
4,826,683 A *   5/1989    Bates ............................ 424/641
6,153,208 A     11/2000   McAtee et al.

FOREIGN PATENT DOCUMENTS

| JP | 2002241310 A | * | 8/2002 |
| JP | 2005082594 A | * | 3/2005 |
| KR | 2001084813 A | * | 9/2001 |

* cited by examiner

*Primary Examiner* — Amy L Clark
(74) *Attorney, Agent, or Firm* — Robert M. Downey, P.A.

(57) ABSTRACT

An oil-based composition for application to mucosal surfaces of the human body provides potent activators of cytoprotective antioxidants. The composition includes the following ingredients: soy oil; coconut oil; orange oil; peppermint oil; aloe vera oil; vitamin E; and may further include jojoba and a preservative. Application of the composition increases expression of antioxidant genes and inhibits proinflammatory action caused by exposure to oxidant pollutants, allergens and other cytotoxins.

4 Claims, 7 Drawing Sheets

COMPOSITION FOR CONTROLLING THE RESPIRATORY EFFECT OF INHALED POLLUTANTS AND ALLERGENS

This application is a Continuation-In-Part (CIP) application of patent application Ser. No. 11/545,720, filed on Oct. 10, 2006 now abandoned, which was based on Provisional Patent Application No. 60/725,050, filed on Oct. 7, 2005.

BACKGROUND OF THE INVENTION

1. Field of the Invention

This invention relates to a composition for application to mucosal surfaces of the human body and, more particularly, to an oil-based composition for protecting against oxidant related tissue inflammation.

2. Discussion of the Related Art

Inflammation in the respiratory system related to tissue oxidant stress is common to a wide variety of airborne exposures and infections. Among well-described environmental exposures are the oxidant pollutants, ozone and nitrogen dioxide, ambient particulate matter, and cigarette smoke (1-6). Many acute and chronic inflammatory diseases of the airways are also associated with oxidant stress and include Chronic obstructive pulmonary disease (COPD), asthma, chronic sinusitis, viral and bacterial infections, and idiopathic pulmonary fibrosis (7-14). Evidence indicates that the upper respiratory system plays an important protective role in many of these types of challenges. In the case of chemical agents, this is achieved by the capture and neutralization of foreign agents in the inspired airstream, limiting their impact on lower airway structures (15). It has also been demonstrated that the nose can serve as a repository for inhaled viral and bacterial pathogens where they can be eliminated or held in check by immune defenses, thereby reducing the risk and/or severity of lower airway infections (16-19).

The effectiveness of the upper respiratory structures in carrying out these host defense activities would appear to depend, in part, upon their own antioxidant capabilities. However, little is known about mechanisms through which nasal antioxidant processes might be augmented and, if so, to what extent such augmentation would be effective as an intervention. As the primary cell of interface between the internal and external environments, the mucosal epithelial cell has long been the focus of much attention as a mediator of external stimuli and facilitator of both innate and acquired immune defenses in the respiratory tract (20, 21). Respiratory epithelial cells are known to initiate the release of a cascade of proinflammatory mediators through redox signaling (8, 22, 23). In addition, these cells have the capacity to exhibit up-regulation of very effective antioxidant defense mechanisms involving the secretion of decoy oxidant targets, as well as the synthesis of a broad spectrum of antioxidants (24, 25). Agents with the ability to enhance antioxidant pathways and interfere with proinflammatory signaling in the upper respiratory epithelial mucosa could enhance the protection afforded by these air passages.

The current studies were undertaken to determine if natural oils with purported antioxidant activities might represent a well-tolerated and potentially effective means through which to enhance inherent protective mechanisms in the nose. For these studies, the actions of a mixture of oils administered by aerosol spray were investigated in human subjects and in human epithelial cell culture systems. The goals were to determine the presence of abrogated pathophysiologic responsiveness in vivo in response to a controlled oxidant challenge in the nose and to develop an understanding of the mechanism through which such effects might be mediated.

SUMMARY OF THE INVENTION

Pulmonary inflammatory diseases involving tissue oxidant stress, such as allergic asthma, COPD, viral and bacterial infections, and sepsis-induced acute lung injury, represent a major health concern. Evidence indicates that antioxidant defenses in the tissues mitigate pulmonary inflammation and that enhancement of these protective pathways can reduce tissue damage and morbidity. However, little is known about the efficacy of oil-based agents in protecting mucosal tissue from oxidant-related inflammation. The present invention is directed to an oil-based composition possessing antioxidant activity for activating cytoprotective mechanisms in mucosal tissue. Pre-treatment with an aerosolized application of the composition to mucosal surfaces significantly reduces inflammatory cell influx following exposure to oxidant pollutant, allergens and other toxins. In particular, treatment increases expression of antioxidant genes in primary and cell line cultures of human airway epithelial cells. In a study, expression of Heme oxygenase-1 was elevated in the nasal mucosa of 9 of 12 subjects after 8 hours following application of the composition to nasal mucosal surfaces. Pretreatment of cultured cells for 15 minutes markedly reduced LPS-induced TNFα expression. These data indicate that oil-based antioxidant agents can provide an effective means for protection against proinflammatory oxidant challenge in the epithelial mucosa of the human upper respiratory tract and other mucosal tissue of the human body.

BRIEF DESCRIPTION OF THE DRAWINGS

For a fuller understanding of the nature of the present invention, reference should be made to the following detailed description taken in conjunction with the accompanying drawings in which.

DETAILED DESCRIPTION OF THE PREFERRED EMBODIMENT

The composition of the present invention comprises a combination of oils containing antioxidant agents. In a preferred embodiment, the composition includes: soy oil; coconut oil; orange oil; peppermint oil; aloe vera oil; vitamin E; and may further include jojoba and a preservative. To determine whether the natural oils of the composition provide cytoprotection, and to determine the mechanisms through which such protection might occur, the following study was undertaken at the Health Effects Assessment Laboratory, Department of Environmental Health Sciences, Johns Hopkins University Bloomberg School of Public Health, Baltimore, Md., under the approval of the Institutional Review Board.

Materials and Methods
Preparation of Test Compounds

The composition of the present invention was the subject of the study. A preferred embodiment of the composition used in the study contains the following components: soy oil—69.18%; coconut oil—20.00%; orange oil—4.90%; aloe vera oil—4.90%; peppermint oil—0.75%; and vitamin E—0.27%. All components of the test formulation are USP-grade and have been individually evaluated and identified by the FDA to fall under the Generally Recognized as Safe classification. This formulation has been demonstrated to be without irritating or inflammatory effects in an in vivo mammalian mucosal test system in studies carried out by North American Science Associates, Inc., an independent FDA-approved safety testing agency. The oil-based preparation was administered as supplied in both in vivo and in vitro experiments, as described below.

For the human nasal studies, sterile water without additives, containing 0.75% peppermint oil as a scented masking agent, was selected for use as the sham test agent. Because saline, itself, has been reported to reduce inflammatory cell number in the nose (26), water was considered to represent an appropriate vehicle against which to compare the oil-based preparation.

Subjects

Nine healthy adult men and women (22 to 40 years of age) were recruited into the ozone exposure study after obtaining informed consent (Table 1). Subjects were excluded if they had a history of chronic respiratory disease, cardiovascular disease or upper respiratory infection during the previous four weeks, if they were "smokers" or if they indicated an inability to sustain light exercise for at least 30 min. "Non-smokers" were defined as those individuals with a lifetime total of fewer than 3 pack-years plus abstinence from smoking of at least one year prior to the study. Subjects were required to refrain from taking prescription and non-prescription anti-inflammatory medications for the week prior to, and for the duration of, the 3-week study period. One subject was removed from the study after the initial nasal lavage indicated the presence of very high numbers of leukocytes in the nose (>100,000/ml), suggesting the presence of a latent upper respiratory infection. A second subject withdrew himself from the study for reasons unrelated to the study.

TABLE 1

Exposure of Healthy Subjects to Ozone

| Subject # | Age (Yrs) | Gender | Arm 1 Cell Counts* | | Arm 2 Cell Counts | |
|---|---|---|---|---|---|---|
| | | | Baseline | Post Ozone | Baseline | Post Ozone |
| 1 | 24 | M | 16077 | 17176 | 9704 | 9594 |
| 2 | 33 | M | 1473 | 3976 | 624 | 310 |
| 4 | 25 | M | 219 | 2044 | 259 | 293 |
| 5 | 30 | F | 250 | 916 | 1786 | 577 |
| 6 | 27 | M | 9032 | 9102 | 3936 | 1355 |
| 7 | 22 | M | 1471 | 2172 | 947 | 512 |
| 9 | 28 | M | 584 | 1100 | 806 | 445 |

*Counts of inflammatory cells expressed as number/ml lavage fluid returned.

Consistent with Institutional Review Board approval and following the same exclusion and consenting procedures described above, 12 additional healthy adult subjects (9 men and 3 women) 22 to 62 years of age were recruited to assess the effects of the oil preparation on baseline anti-oxidant gene expression in the nasal epithelium (Table 2).

TABLE 2

Nasal HO-1 Gene Expression in Healthy Subjects

| Subject # | Age (Yrs) | Gender | Fold Change from Baseline* | | Oil Fold Change from Sham |
|---|---|---|---|---|---|
| | | | Sham Spray | Oil Spray | |
| 1 | 33 | M | 0.247 | 2.732 | 11.08 |
| 2 | 62 | M | 0.297 | 1.283 | 4.32 |
| 3 | 31 | M | 0.758 | 0.620 | 0.82 |
| 4 | 34 | F | 2.099 | 15.348 | 7.31 |
| 5 | 41 | M | 0.330 | 4.532 | 13.73 |
| 6 | 24 | F | 1.040 | 0.285 | 0.27 |
| 7 | 60 | M | 0.432 | 0.914 | 2.11 |
| 8 | 27 | M | 0.859 | 0.245 | 0.29 |
| 9 | 31 | M | 1.778 | 3.387 | 1.90 |
| 10 | 42 | M | 0.651 | 1.079 | 1.66 |
| 11 | 41 | F | 1.181 | 3.249 | 2.75 |
| 12 | 33 | M | 0.829 | 1.580 | 1.91 |
| Median | | | 0.793 | 1.432† | 2.01 |

*Data calculated as fold change after normalization to corresponding β-actin expression.
†Statistically significant from sham (P = 0.027).

Cells

BEAS-2B Cells. Cells of the BEAS-2B human bronchial epithelial cell line were obtained from the American Type Culture Collection (ATCC, Bethesda, Md.). Cultures were expanded by growth on 100 mm plastic dishes in Ham's F-12 medium (Biofluids, Rockville, Md.) and seeded on 6- or 12-well Falcon filter inserts (0.4 μm pore size; Becton Dickinson, Franklin Lakes, N.J.) and grown to confluence with the same medium above and below prior to treatment, as described for HBE cells below.

Primary Human Bronchial Epithelial (HBE) Cells. Cells were isolated from the airways of lungs obtained from healthy, non-smoking organ donors. Following overnight digestion of airway tissues at 4° C. in 0.1% protease in Ham's F-12 medium containing penicillin (100 U/ml), streptomycin (100 μg/ml), fungizone (2.5 μg/ml) and gentamicin (50 μg/ml), the protease was neutralized by the addition of 10% soybean trypsin inhibitor and the epithelial cells were freed from the tissue by agitation and isolated by centrifugation. The washed epithelial cells were then seeded, at a density $\geq 1.6 \times 10^4$ cells/cm$^2$, onto collagen-coated dishes in serum-free Bronchial Epithelium Growth Medium (BEGM), as described by Bemacki and colleagues (27). This modified (28) LHC Basal Medium (Biofluids, Rockville, Md.) contained [all sources Sigma, unless otherwise indicated] insulin (5 μg/ml), hydrocortisone (0.072 μg/ml), human epidermal growth factor (25 ng/ml, Upstate Biotechnology), triiodothyronine (6.5 ng/ml), retinoic acid ($5 \times 10^{-8}$M), transferrin (10 μg/ml, Gibco), epinephrine (0.6 μg/ml), phosphoethanolamine (0.5 μM), ethanolamine (0.5 μM), bovine pituitary extract (10 μg/ml, Upstate Biotechnology), bovine serum albumin (0.5 mg/ml), calcium (0.11 mM), selenium (30 nM), manganese (0.6 nM), silicon (0.5 μM), molybdenum (1.0 nM), vanadium (5.0 nM), nickel (0.5 nM), tin (0.5 nM), zinc (3.0 μM), iron (0.15 μM), magnesium (60 nM), penicillin (100 U/ml), streptomycin (100 μg/ml), and amphotericin B (0.25 μg/ml).

Upon reaching confluence, the epithelial cells were transferred to Human Placental Collagen (Sigma, Type VI)-coated 6-well Falcon filter inserts and grown to confluence with BEGM above and below the cells, as previously described in detail (29). When confluent, apical medium was removed from above the cultures and the medium below the inserts was changed to Air-Liquid Interface (ALI) medium consisting of LHC Basal Medium:DMEM-H (Gibco) (50:50) containing the same concentrations of additives as BEGM with the exception that the concentration of epidermal growth factor was reduced to 0.63 ng/ml, and amphotericin B was omitted. The cultures were maintained at the air-liquid interface for 21 days prior to treatment to allow full mucociliary differentiation. To confirm the epithelial cell composition of primary cultures derived from this protocol, cells were stained using a monoclonal mouse antibody against human Epithelial Specific Antigen (NCL-ESA, Vector Laboratories, Burlingame, Calif.) and mouse IgG$_1$ as control. The presence of antigen on the cell surfaces was visualized using a Vectastain ABC kit with DAB as a substrate followed by counterstaining with hematoxylin. Similarly stained cells of the WI-38 fibroblast line served as negative controls.

Treatment and Exposure of Subjects to Ozone

The human subjects component of the study was carried out in the Health Effects Assessment Laboratory (HEAL) in the Department of Environmental Health Sciences of the Bloomberg School of Public Health. One day prior to ozone exposure in each of the two arms of the protocol, subjects underwent nasal lavage to confirm that baseline inflammatory cell concentrations fell within normal limits (<20,000 cells/ml). On the next day, either the saline control preparation containing 0.75% peppermint oil as a masking agent (Arm 1) or the oil-based test agent (Arm 2), were administered in a single-blinded manner as a single 50 μl application in each nostril using a metered spray applicator (model VP7/50 18/415+poussoir 232 NA/B) manufactured by Valois, Le Vaudreuil, France. Immediately following nasal treatments, subjects were exposed to 0.25 ppm $O_3$ for 120 min. with alternating 30 min periods of rest and light exercise consisting of slowly walking on a treadmill. Exposures took place in a temperature- and humidity-controlled chamber as previously described (30). To optimize upper respiratory targeting, subjects were visually monitored after being instructed to chew gum with a closed mouth for the duration of the exposure period. Eighteen hours following exposure, subjects again underwent nasal lavage to assess post-exposure inflammation. After a 7-10 day washout period, the 3-day treatment and exposure were repeated in Arm 2 of the protocol, associated with the application of the second of the two nasal spray preparations.

Assessment of Nasal Inflammation

Nasal lavage was carried out according to a standardized procedure. With the subject seated in a chair and the head tilted backwards, 5 ml of 37° C. Ringer's lactate was instilled by pipette into each nostril. After 5-10 seconds, the head was brought forward and the fluid expelled into a basin by gentle blowing. This procedure was repeated 4 times. Following centrifugation, the cells from all 4 tubes were pooled by resuspension in phosphate buffered saline for cellular analysis.

Counts of inflammatory cells were made using a hemocytometer and calculated as total inflammatory cells per ml of nasal lavage return. Return volumes, which averaged 84% of the 40 ml instilled volume, were very consistent within each subject and were used to normalize the inflammatory cell return.

Nasal symptoms prior to and at eighteen hours post exposure in each of the two arms were scored following a standard procedure by having the subjects make a mark on a horizontal line indicating the level of the symptom described, with the least sensation at the far left and the most at the far right. Scores were determined by measuring the distance in mm from the left end of the line and the change in numerical values between the two arms were compared.

Assessment of Nasal Epithelial Gene Expression

Collection of nasal mucosal epithelial cells was made from the upper and lower aspects of the inferior medial turbinates of the right and left nostrils using a nasal mucosal curette (Rhino-probe®). Epithelial biopsy samples were taken prior to and 8 hours following administration of the oil-based test agent or the scented control preparation utilized in the ozone study. Using a metered spray applicator, 50 microliters of each of the two agents was administered in a single-blinded and random manner to one or the other of the two nostrils. Using this design, each turbinate provided its own baseline value for gene expression and the two agents were tested simultaneously in the same individual.

Treatment of Cells in Culture

After ensuring that the surfaces of human primary and BEAS-2B epithelial cell cultures were free of liquid, 200 μl of medium (HBE cell control) or HBSS (BEAS-2B control) or oil preparation were added to the apical surfaces and evenly distributed by rotation. The cultures were returned to the incubator for 15 min. prior to removal of the treatment fluids by suction. The surfaces were then gently washed twice with 500 μl of warmed (37° C.) HBSS, and the cultures were returned to the incubator for the designated periods of time prior to extraction of RNA or protein. In two series of experiments, control and oil-treated cells underwent further challenge at 12 hours with lipopolysaccharide (LPS, 3 μg/ml, *Escherichia coli*, serotype 055.B5-Sigma.) for 4 hours prior to RNA extraction.

Determination of Gene and Protein Expression

Real Time RT-PCR. Total RNA was extracted from the cells using the RNeasy kit (Qiagen) and was quantified by UV absorbance spectrophotometry. The reverse transcription reaction was performed by using the high capacity cDNA synthesis kit (Applied Biosytems) in a final volume of 20 μl containing 1 μg of total RNA, 100 ng of random hexamers, 1× reverse transcription buffer, 2.5 mM $MgCl_2$, 1 mM dNTP, 20 units of multiscribe reverse transcriptase, and nuclease free water. Quantitative real time RT-PCR analyses of Human Heme oxygenase (HO-1), NADPH dehydrogenase, quinone-1 (NQO1), glutamate cysteine ligase-modulatory subunit (GCLm), glutamate cysteine ligase-catalytic subunit (GCLc), glutathione-S-reductase (GSR) and tumor necrosis factor alpha (TNFα) were performed by using assay on demand primers and probe sets from Applied Biosystems. Assays were performed by using the ABI 7000 Taqman system (Applied Biosystems). β-ACTIN was used for normalization.

Western Blot Analysis. To obtain total protein lysates, cells were lysed in RIPA buffer containing Halt Protease Inhibitor cocktail (Pierce, Rockford, Ill., United States) and centrifuged at 12,000 g for 15 min at 4° C. Protein concentrations of the supernatant were measured using Bio-Rad protein assay (Bio-Rad, CA). For immunoblot analysis, 100 μg of total protein lysate was resolved on 12% SDS-PAGE gels. Proteins were transferred onto PVDF membranes and blocked with PBS-Tween (0.1% Tween-20 in PBS, pH 7.2) supplemented with 5% low fat milk powder (w/v) for 2 h at room temperature. All primary antibodies were diluted in PBS-Tween (0.1%) with 5% nonfat dry milk and incubated overnight at 4° C. Following antibodies were used for immunoblotting: anti-HO1 (Abcam), anti-NQO1 (Novus Biologicals), anti-GCLm, and anti-GAPDH (Imgenex, Sorrento Valley, Calif., United States). After washing the primary antibody, the membranes were incubated with horseradish peroxidase conjugated anti-rabbit or anti mouse antibody (1:2500 in 0.1% Tween-20, with 5% low fat milk powder (w/v) for 1 hr at room temperature. Membranes were again washed with PBS-Tween (0.1%) and secondary antibodies were visualized by enhanced chemiluminescence detection system (Amersham Biosciences, NJ).

Statistics

Nasal lavage and biopsy data were tested for differences between control and oil-treatments using paired-t analyses. In instances of a lack of normality, the Wilcoxon Signed Rank Test was used. In all cases, P values <0.05 were considered significant. Statistical analyses were carried out with SigmaStat Statistical software (Jandel Scientific, San Rafael, Calif.).

Results

Ozone-Induced Nasal Inflammation

Figure 1:
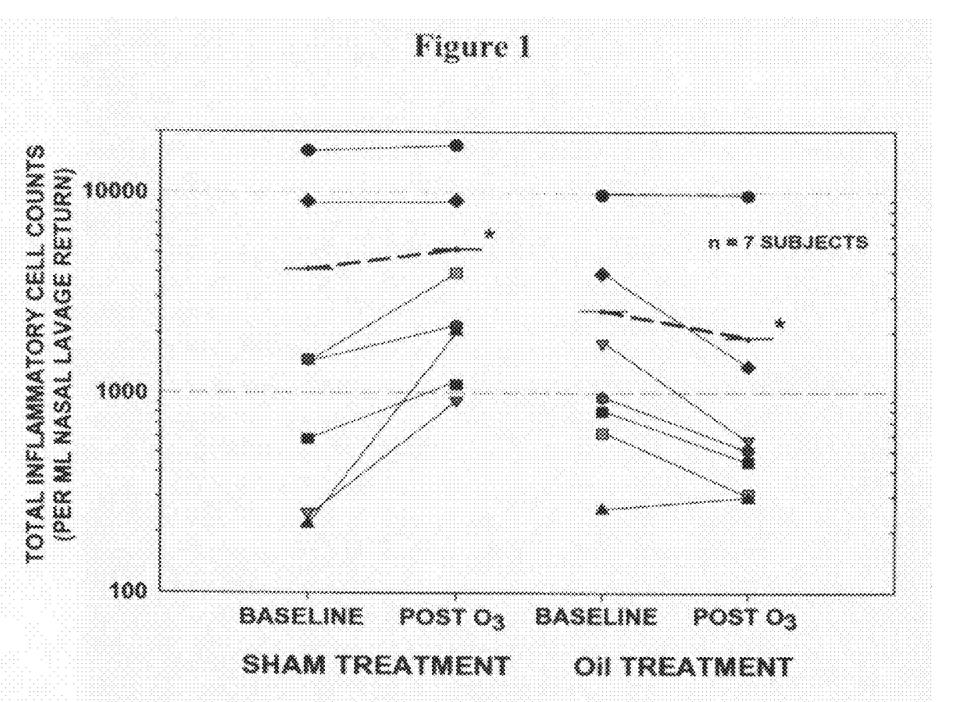
FIG. 1 is a graph illustration showing a comparison between test subjects under a sham treatment other test subjects under treatment using the oil-based composition of the present invention. Individual data showing the upper respiratory inflammatory responses of subjects exposed to ozone (0.25 ppm, 2 hr) when pretreated with 50 μl of saline (sham) or a mixture of natural oils administered by aerosol spray to each nostril. Each subject is represented by the same symbol in both arms of the study. Points connected by dashed lines represent means of each group. * indicates significant difference from baseline (P<0.05) by paired t analysis.
Figure 2:
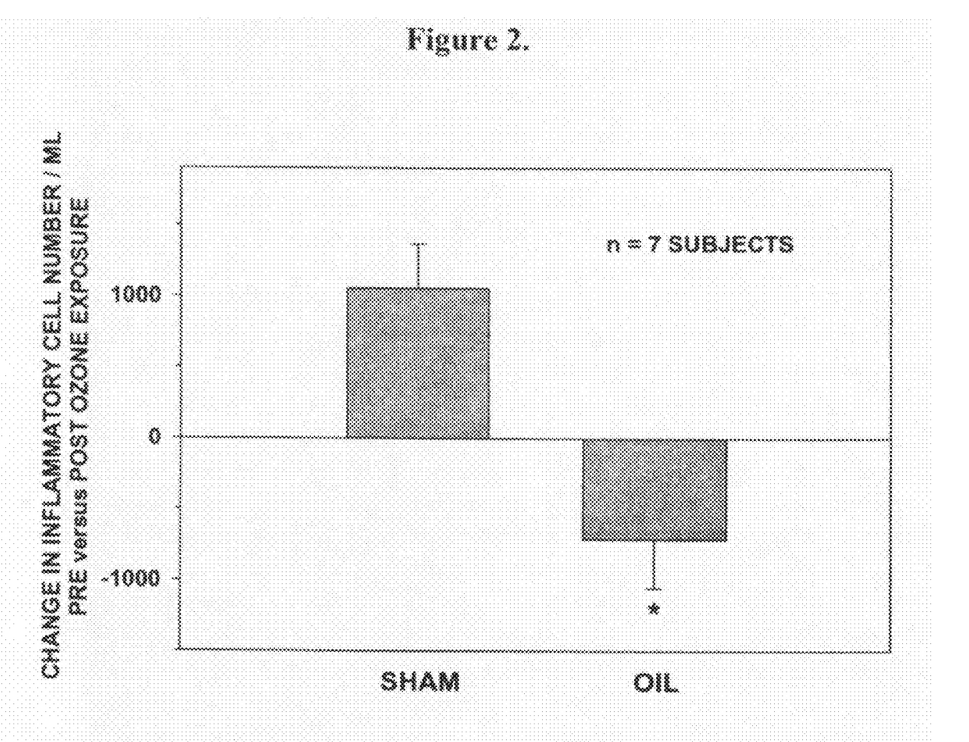
FIG. 2 is a bar graph showing a comparison of the effects of the sham treatment and treatment with the oil-based composition, and particularly the change in inflammatory cell number in the nose in response to ozone exposure. * indicates significant difference from sham (P<0.001) by paired t analysis.

In the majority of individuals, the typical response of exposure of the upper and lower respiratory epithelium to ozone is inflammation and an influx of inflammatory cells, especially PMNs, to mucosal and luminal regions. This process is mediated by the oxidant stress-related release of pro-inflammatory mediators by epithelial cells. As a means to determine if administration of the oil preparation could afford protection against this example of oxidant-induced inflammation in the upper respiratory system, the effect of pretreatment with the oil was compared to that of sham control. As assessed by nasal lavage, controlled exposure to 0.2 ppm ozone for 2 hrs resulted in nominal to 9-fold increases in inflammatory cell influx in 7 seven subjects undergoing sham pretreatment (Table 1; FIG. 1). Differential cell counts showed these cells to be >96% PMNs with occasional mononuclear and infrequent eosinophilic cells. This increase in inflammatory response was statistically significant within this treatment group. In the same subjects undergoing pretreatment with the aerosolized oil preparation, the ozone-induced increase in inflammatory cells in the nasal lavage was completely inhibited, Furthermore, cell numbers were statistically reduced below those present prior to the exposure (FIG. 1), suggesting that a mechanism involving direct reduction of inflammatory signaling was initiated in cells undergoing oil treatment. Comparison of the two treatment regimens demonstrated that administration of the oil preparation significantly reduced the response of the subjects to the pro-inflammatory effects of ozone exposure (FIG. 2). Average lavage return was not different in the two treatment arms (sham: 33.4 ml; oil: 33.7 ml).

Consistent with reduced levels of tissue inflammation as assessed by cellular influx, symptom scores for "ease of airflow through the nose" were significantly greater in ozone-exposed subjects following pretreatment with the oil preparation when compared to sham treatment (P<0.05).

Antioxidant Expression in Primary HBE Cells

Figure 3:
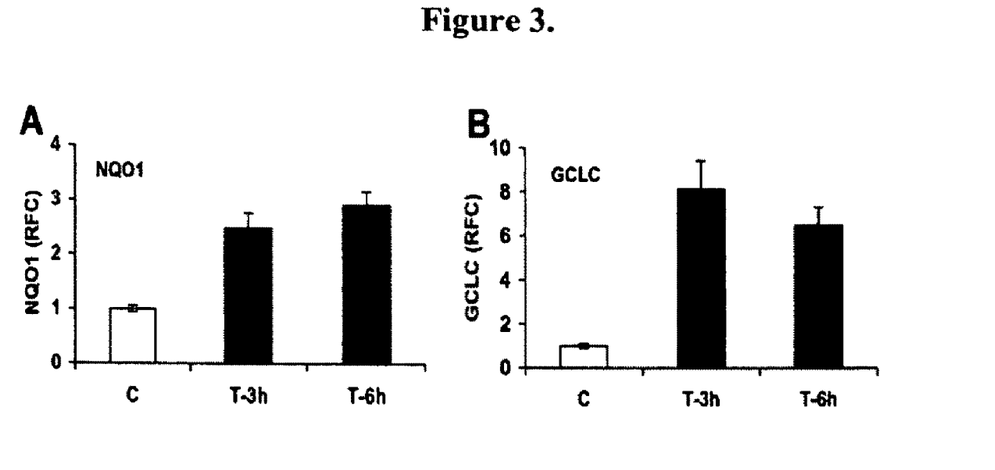
FIG. 3 shows two graphs, Graph A and Graph B, illustrating how treatment of fully-differentiated primary human respiratory epithelial cells with the oil preparation increases expression of antioxidant genes NQ01 and GCLm. RNA was isolated from cells grown at the air-liquid interface at 3 hr or 6 hr following treatment for 15 min with the oil or medium (control). Data are presented as fold change from time-matched sham controls after normalization to expression of actin. Data are expressed as mean±SD of triplicate cultures.

In order to pursue the premise that the protection afforded by the oil treatment in the nose extended beyond the establishment of a physical barrier to the ozone, primary HBE cells were selected as a surrogate for the nasal cells. HBE cells were grown to full mucociliary differentiation at the air-liquid interface exposed to the oil preparation or medium control for 15 min. followed by washing ×3 with warmed HBSS. RNA was extracted from the cultures at the designated times and treated cells were compared to their corresponding controls. As shown in FIG. 3A, expression of NQO1 increased by more than 2-fold at 3 hours post treatment and remained high at 6 hours. Likewise, the catalytic subunit of GCL (GCLc) was up-regulated at 3 hours by approximately 8-fold and remained high at the 6 hour time point (FIG. 3B). These observations support the notion that the oil preparation may have had a direct effect on airway epithelial cells when applied to the nose that was related to an activation of cellular antioxidant defense mechanisms.

Kinetics of Gene and Protein Expression

Figure 4:
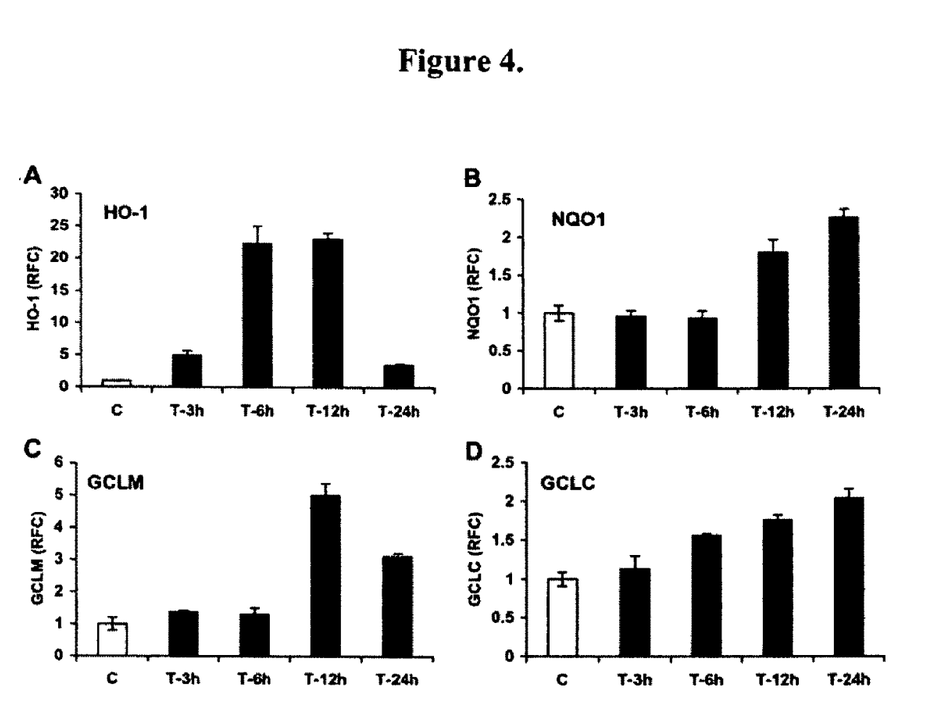
FIG. 4 shows four Graphs A-D illustrating how treatment of cells with the oil-based composition of the invention increases expression of oxidant-protective pathways with differing activation kinetics. The graphs show time-course of expression of antioxidant genes HO-1, NQO1, GCLm, and GCLc in cells of the BEAS-2B human bronchial epithelial line at designated times following treatment. Data are presented as fold change from time-matched HBSS controls after normalization to expression of actin. Presented are results from one of two separate experiments showing similar data. Results are expressed as mean±SD of triplicate cultures.

To describe a more complete profile of the kinetics of antioxidant gene expression induced by 15 minutes of oil treatment in human airway epithelial cells, cells of the BEAS-2B line were treated and extracted at 3, 6, 12, and 24 hours following treatment. As seen in FIG. 4A, HO-1 exhibited a 5-fold increase in expression at 3 hours that reached more than 20-fold by 6 hours. After remaining at this level for up to 12 hours, HO-1 expression returned toward its time-matched control by 24 hours. In contrast, neither GCLc nor NQO1 increased by more than 1.5-fold until 6 and 12 hours post treatment, respectively (FIG. 4B,D). The onset of response of these genes was thus delayed from that observed in the primary cells; however, by 24 hours, expression of both GCLc and NQO1 was 2-fold greater than time-matched control cells. Expression of the modulatory sub-unit of GCL was likewise delayed relative to HO-1, but was 5-fold increased by 12 hours and remained 3-fold elevated at 24 hours post treatment (FIG. 4C).

Figure 5:
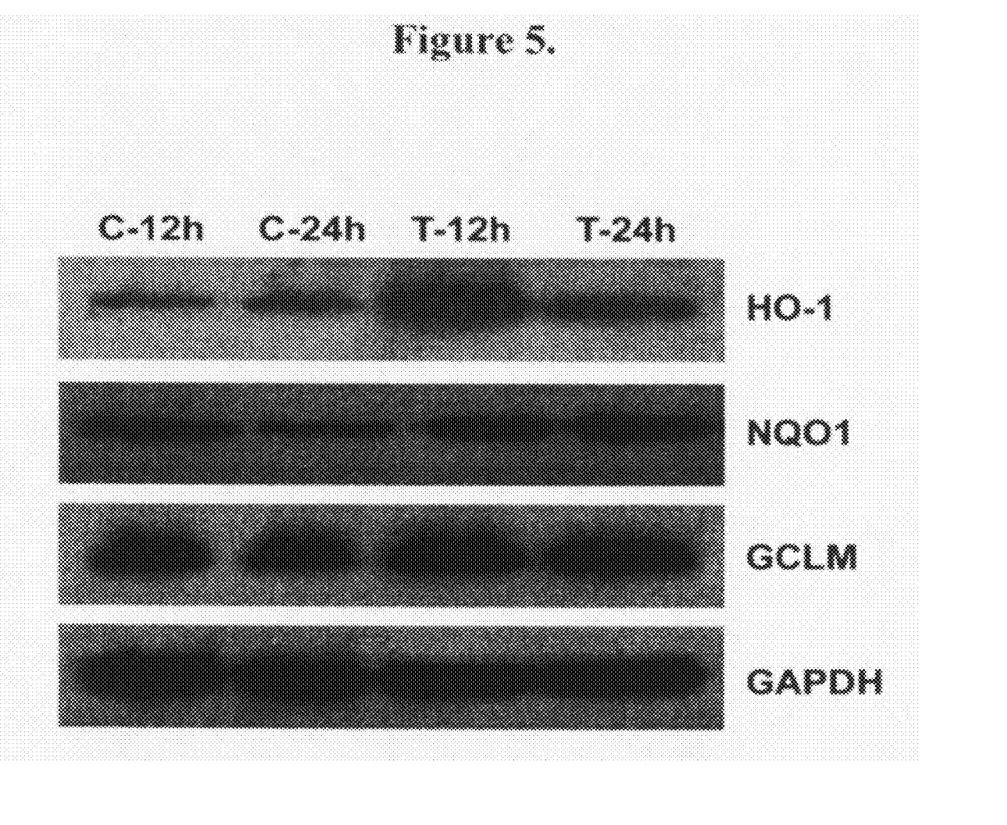
FIG. 5 is an immuoblot demonstrating expression of HO-1, NQO1, and GCLm, proteins at 12 and 24 hrs following 15 min treatment of BEAS-2B cells with the oil-based composition or time-matched HBSS control. Shown is one of two separate experiments giving similar results.

To confirm translation of antioxidant gene signaling to product formation, Western blot analysis of HO-1, NQO1, and GCLm was carried out. At 12 and 24 hours, protein synthesis for these proteins was increased in oil-treated versus control cells, at levels generally consistent with relative gene expression at these times (FIG. 5).

Nasal Epithelial Antioxidant Gene Expression In Vivo

Figure 6:
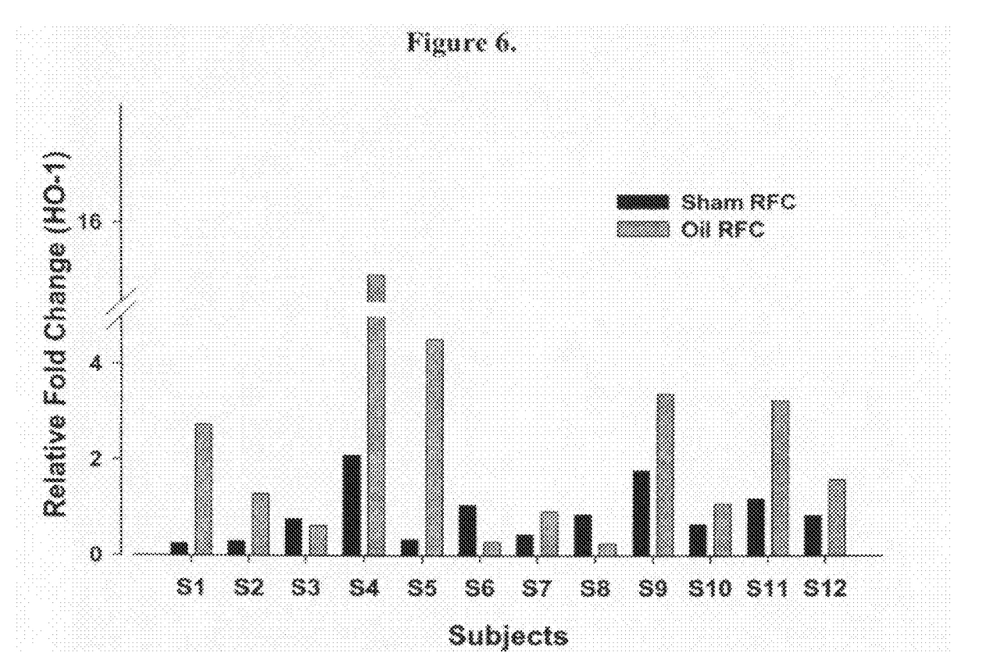
FIG. 6 is a bar graph comparing the administration of the sham treatment and the oil-based composition of the present invention to the nasal passages by aerosol spray stimulates antioxidant gene expression in the nasal epithelial mucosa. Change in HO-1 expression in paired bilateral nasal epithelial biopsies from individual subjects 8 hours following sham treatment or treatment with the oil preparation. Data presented as fold change from pre-treatment baseline values in each pair of tissues.

Nasal mucosal biopsies were taken from 12 healthy volunteers to determine if the up-regulation of antioxidant gene expression in response to the oil preparation seen in cultured cells was also evident in the nasal epithelial mucosa. Biopsies of cells were taken from the inferior medial turbinates of the right and left nasal passages prior to and 8 hours following treatment. Because of its rapid onset of expression in BEAS-2B cells, HO-1 was selected as the target gene. In 9 of the 12 subjects, HO-1 expression in oil-treated turbinates increased by at least 1.5-fold above sham control and, in 6, expression was increased more than 2-fold at the 8 hour time point (Table 2). In all but 3 of 12 subjects, expression was higher in oil-treated turbinates. Overall, paired analysis of the change in fold expression between sham-treated and oil-treated turbinates using the Wilcoxon Signed Rank Test demonstrated a significant difference (P<0.03). FIG. 6 depicts the individual subjects' HO-1 data expressed as fold change in sham and oil test agent from that seen in the corresponding baseline.

Inhibition of Endotoxin-Induced Pro-Inflammatory Gene Expression

Figure 7:
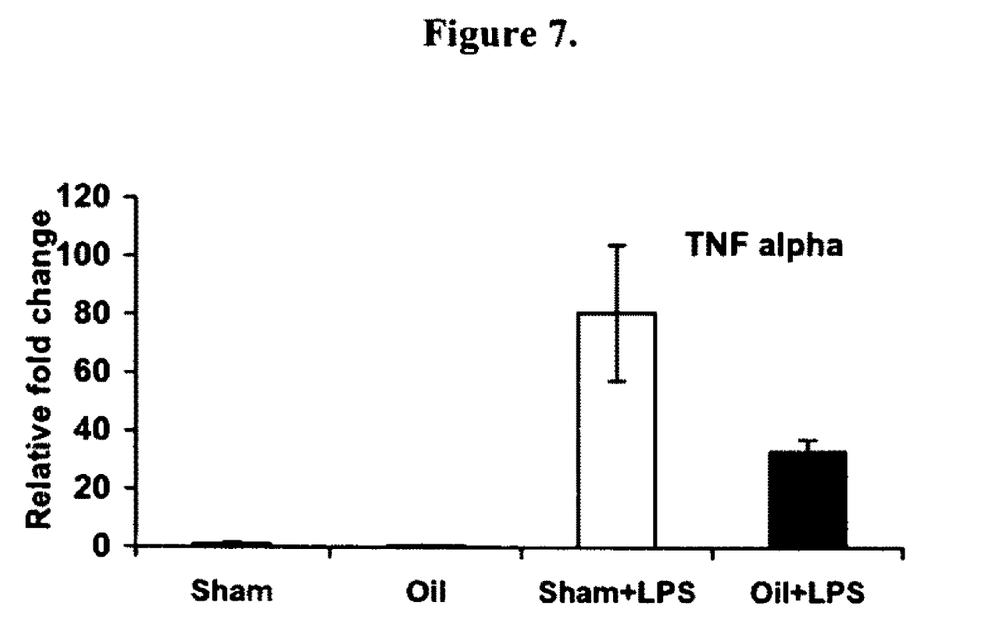
FIG. 7 is a bar graph showing how pretreatment with the oil-based composition attenuates LPS-induced expression of TNFα. BEAS-2B cells were pretreated with the natural oil mixture for 12 hr and then stimulated with vehicle or LPS (3 ug/ml) for 4 hr. TNFα transcript levels were measured using real time RT-PCR. Data are presented as fold change from time-matched HBSS controls after normalization to expression of actin. Presented are results from one of two separate experiments showing similar data. Results are expressed as mean±SD of triplicate cultures.

In order to confirm in an oxidant-driven inflammatory system different from ozone exposure that the oil test preparation was able to mitigate proinflammatory signaling, bacterial endotoxin was administered to human airway epithelial cells. Twelve hours following a 15 minute pretreatment with HBSS (control) or the oil preparation, cells were exposed to 3 µg/ml of LPS for 4 hours. Inflammatory signaling was assessed by determining expression of TNFα, the gene that encodes this potent proinflammatory cytokine. There was no difference in relative expression between control cells and those treated with the oil-based agent alone (control: 1.1±0.54; oil: 0.51±0.19, for TNFα). At a concentration of 3 µg/ml, LPS in sham-pretreated cultures increased expression of TNFα by 81-fold, compared to that in unchallenged controls (FIG. 7). Compared to control, oil treatment decreased LPS-induced proinflammatory signaling by more than 50% (33-fold).

Discussion

The present study was designed to determine if naturally-occurring oils with antioxidant properties could be utilized to provide protection against proinflammatory challenges to the upper respiratory tract. In addition to the palliative effects of the oils themselves on the nasal epithelial mucosa, the presence of oil constituents with antioxidant activity could presumably have a direct effect on mucosal cells, increasing their innate defense against agents that induce inflammation through oxidant-related pathways.

Exposure to ozone has long been known to lead to an inflammatory response in the upper and lower respiratory tracts characterized by the influx of PMNs (4, 31). Under conditions of controlled exposure of subjects to 0.25 ppm ozone for 2 hours in the present study, this response was observed in the upper respiratory tract. Pretreatment of the nasal passages by aerosol spray with a natural oil preparation inhibited the inflammatory response. Because of the reactive target that oil might present to inhaled ozone, some degree of protection, at least early in the 2 hour exposure period, could have been provided by a simple "barrier" effect (32). If this were the case, it might be expected that administration of the oil would reduce or eliminate the ozone-induced inflammatory response. However, the data demonstrated that PMN levels in the nasal lumen at the 24 hour post-exposure time point were significantly reduced below those in the pre-exposure samples. This observation suggests that proinflammatory signaling was abrogated in the nasal mucosa by the treatment, possibly through mechanisms involving increased intracellular antioxidant activity leading to reduced inflammatory drive. In addition, it indicates that this activity persisted in the tissue, at least to the sampling point 24 hours after the ozone exposure period.

Studies conducted in human primary and cell line airway epithelial cells in culture confirmed the direct anti-inflammatory effects of the oil preparation. Primary airway epithelial cells of the upper and lower respiratory tract grown at the air-liquid interface undergo full mucociliary differentiation and closely mimic the structural and functional characteristics of these cells in vivo (27, 28). In both the primary cultures and cells of the commonly-used BEAS-2B airway epithelial line, up-regulation of expression of anti-oxidant genes was demonstrated.

Ozone has been shown to stimulate the influx of PMNs into the airway lumen as early as 1 hr following exposure (33). Since, in the present study, initiation of oxidant-induced signaling within the epithelium was limited to the 2 hour exposure period during which time cellular influx would be initiated, it might be reasonable to assume that the active agents in the oil preparation provided at least a part of their mitigating effect at an early time following administration. This assumption would be consistent with the induction of rapidly-responding antioxidant enzymes, such as HO-1, the genetic expression of which was increased by 5-fold in cultured cells within 3 hours of treatment and was found to exhibit elevated expression in the nasal epithelium of responding subjects at 8 hours. Thus, the activation of multiple antioxidant protective enzymes with differing kinetics of expression may lead to an antioxidant and anti-inflammatory protective effect that has both rapid and prolonged components, as suggested by the in vitro time-course data.

The five antioxidant genes investigated in this study, HO-1, GCLc, GCLm, GSR and NQO1, are known to have a common antioxidant response element (ARE) in their promoters and are expressed in an Nrf2-dependent manner. The basic leucine zipper (bZip) transcription factor, Nrf2, acting via an antioxidant/electrophile response element, regulates the expression of several antioxidant enzymes and maintains cellular redox homeostasis (34). Among the antioxidant genes studied, HO-1 induction in response to oil treatment was the most rapid and dramatic. Heme oxygenase catalyzes the rate limiting steps of heme oxidation to biliverdin, carbon monoxide and iron. Biliverdin is rapidly converted to bilirubin, a potent endogenous antioxidant. Three isoforms of heme oxygenase have been reported: the inducible HO-1 and the constitutively expressed HO-2 and HO-3. An increasing number of studies implicate HO-1 in the regulation of inflammation. The induction of HO-1 has been demonstrated in many models of lung injury including hyperoxia, endotoxemia, bleomycin, asthma, acute complement-dependent lung inflammation, and heavy metals (35, 36).

In an in vitro model of oxidative stress using pulmonary epithelial cells stably transfected to overexpress HO-1, Lee et al. (37) demonstrated that these cells exhibited increased resistance to hyperoxic cell injury. In studies by Petrache et al. (38) and Soares et al. (39), HO-1 also prevented TNF-α-mediated apoptosis in fibroblasts and endothelial cells, respectively. Such findings further substantiate the involvement and importance of HO-1 in cytoprotection.

Otterbein and colleagues (40-42) have demonstrated that HO-1 induction correlated with cytoprotection against oxidative stress in vivo. Using hyperoxia as a model of acute respiratory distress syndrome in rats, they demonstrated that the exogenous administration of HO-1 by gene transfer could confer protection against oxidant-induced tissue injury.

Adenoviral gene transfer of HO-1 (Ad5-HO-1) into the lungs of rats resulted in increased expression of HO-1 and, importantly, induced a marked resistance to hyperoxic lung injury (42, 43). Rats treated with Ad5-HO-1 showed reduced levels of hyperoxia-induced pleural effusion, neutrophil alveolitis, and bronchoalveolar lavage protein leakage. Furthermore, rats treated with Ad5-HO-1 showed increased survivability in the presence of hyperoxic stress versus those treated with the vector control virus (42, 43).

Another important antioxidant, NQO1, is primarily expressed in tissues requiring a high level of antioxidant protection, such as the epithelial cells of the lung, breast, colon, and vascular endothelium. High basal levels of NQO1 expression suggest that this molecule may play a key role in establishing the antioxidant capacity in these cells (44). Oxidant pollutants, including diesel exhaust particles, induce NQO1 expression which plays a role in mitigating pollutant-enhanced IgE responses (45). Furthermore, overexpression of phase II enzymes, including NQO1, inhibited IgE production and supports the concept that chemical upregulation of these enzymes may represent a chemopreventative strategy in airway allergic diseases (45). Thus, the oil-induced inductions of NQO1 and related antioxidants may have broader implications for protection of the respiratory mucosa against pollutant-related proallergenic effects in susceptible individuals.

Cellular antioxidant defenses can counter inflammation by limiting the levels of ROS generated. Expression of genes involved in glutathione biosynthesis (GCLc, GCLm, and GSR) and other antioxidants like HO-1 and NQO1 were significantly upregulated in response to oil pretreatment. Further, pretreatment of BEAS-2B cells with the oil greatly suppressed TNFα activation in response to LPS treatment. Lower levels of GSH have been reported to augment activation of the proinflammatory transcription factor, NF-κB, (46). A protective role of GSH peroxidase in LPS-induced inflammation has also been previously reported (47). In addition, induction of HO-1 may exert anti-inflammatory functions through the generation of carbon monoxide and has been shown to inhibit the expression of cytokines (35). These results imply that certain components present in the oil mixture may maintain the redox equilibrium by regulating GSH and other antioxidant enzymes and that this mechanism may be partially responsible for alleviating LPS-induced inflammation (47).

Although seemingly unrelated in terms of their sources and the nature of their interactions with the respiratory system, many environmental challenges share the development of cellular oxidative stress as a common pathway for cell activation and, in some cases, cytotoxicity. Such challenges include virus and bacterial infection (10, 48), allergen challenge (49), and exposure to common gaseous and particulate air pollutants (50, 51), tobacco smoke (52), and bacterial endotoxin (53). It is important to note that many of these diverse exposures occur in combination and may synergize to produce greatly amplified responses within epithelial cells of the respiratory tract. For example, in a study of human bronchial epithelial cells in culture, it was observed that the consequences of oxidant stress induced by the oxidant pollutants ozone or nitrogen dioxide in combination with rhinovirus infection resulted in release of the proinflammatory mediator, IL-8, at levels as much as 2.5-fold greater than those predicted by the single exposures (3). Thus, targeting oxidant-related pathways leading to inflammatory responses in the upper respiratory tract may offer a means to provide cytoprotection against a range of environmental challenges to those tissues. Such antioxidant strategies may be especially beneficial in individuals who have reduced or absent phase II enzyme activity, such as may occur with certain genetic polymorphisms.

The present study demonstrates that a mixture of natural oils with purported antioxidant properties was capable of reversing the nasal inflammatory response to ozone exposure in healthy human subjects in a manner that persisted for up to 18 hours. In human airway epithelial cells in culture, short duration treatment resulted in increases in the expression of a range of antioxidant genes with both rapid response and late activation profiles. Short duration of exposure to oil had long lasting effect compared to aqueous-based agents, such as sulforaphane (54). It may be that the prolonged antioxidant effect resulting from a relatively short 15 minute treatment time is due to the rapid integration of the active component(s) into the cell membrane that acts as a repository for sustained release into the cell. It will be important to determine if the presence of a lipid-based carrier plays a role in increasing the duration of antioxidant pathway activation.

Considerable interest has focused on the protective role of Nrf2-dependent pathways in a variety of diseases, including those of the respiratory, gastrointestinal, neurological, and nephrological systems, as well as immune and metastatic diseases (34, 47, 55, 56). The observed increase in HO-1, NQO1, GCLm, GCLc and GSR expression, genes that are down-stream of Nrf2 signaling, suggests that treatment with the oil preparation resulted, at least in part, in the activation of this transcription factor within the respiratory epithelial cells.

In summary, the present study demonstrates that a mixture of natural oils proposed to have antioxidant properties was able to abrogate the inflammatory response to the oxidant pollutant, ozone, in the nasal passages of healthy subjects. This oil preparation stimulated the expression of several early and late responding antioxidant genes in human respiratory epithelial cells in culture. The most rapidly-responding of these genes, HO-1, was determined to undergo increased expression in the nasal tissues of subjects treated with the oil. In total, these novel data offer evidence that delivery of oil-based agents may represent an effective means by which to increase the activity of antioxidant pathways and provide anti-inflammatory protection within the nasal epithelial mucosa. In addition, the ability of oil pre-treatment to inhibit the pro-inflammatory action of subsequent bacterial endotoxin exposure of human respiratory epithelial cells suggests the potential usefulness of the preparation in mitigating a broader array of inflammatory and cytotoxic exposures to the upper respiratory system.

The respiratory epithelial mucosa is one example of a tissue that plays a key role at the interface of the external and internal environments. Respiratory epithelial cells are central to the success of adaptive responses that have oxidant-stress related components, such as those associated with pollutant exposures, viral infections and allergic challenge. The identification of naturally-occurring products, such as the oil preparation tested here, that are potent activators of cytoprotective mechanisms within these cells will expand our opportunities to develop new tools for preventive and therapeutic intervention.

While the present invention has been shown and described in accordance with preferred and practical embodiments thereof, it is recognized that departures from the instant disclosure are fully contemplated within the spirit and scope of the invention.

What is claimed is:

1. A composition for application to mucosal surfaces in the nose for treating nasal inflammation, said composition comprising:

soy oil in an amount of 69.18% by weight of the composition;

coconut oil in an amount of 20.0% by weight of the composition;

orange oil in an amount of 4.9% by weight of the composition;

peppermint oil in an amount of 0.75% by weight of the composition; and aloe vera oil in an amount of 4.9% by weight of the composition.

2. The composition of claim 1 further comprising: Vitamin E in an amount of 0.27% by weight of the composition.

3. The composition of claim 2 further comprising jojoba.

4. The composition of claim 2 further comprising a preservative.

* * * * *